United States Patent [19]

Finer et al.

[11] Patent Number: 4,646,341
[45] Date of Patent: Feb. 24, 1987

[54] CALIBRATION STANDARD FOR X-RAY FLUORESCENCE THICKNESS

[75] Inventors: Paul Finer, Roslyn Heights; Robert O. Wahl, Sound Beach; William Silverman, Melville, all of N.Y.

[73] Assignee: UPA Technology, Inc., Syosset, N.Y.

[21] Appl. No.: 716,986

[22] Filed: Mar. 28, 1985

[51] Int. Cl.[4] ............... G01N 23/06; G01B 15/02; G01D 18/00
[52] U.S. Cl. ............... 378/207; 378/56; 378/48; 378/50
[58] Field of Search ............... 378/50, 53, 56, 48, 378/79, 206–208, 89; 250/440.1, 252.1; 427/437, 405

[56] References Cited

U.S. PATENT DOCUMENTS

| | | | |
|---|---|---|---|
| 2,711,481 | 6/1955 | Phillips | 378/32 |
| 3,307,036 | 2/1967 | Bouvelle | 378/79 |
| 4,150,288 | 4/1979 | Inoue et al. | 378/207 |
| 4,162,528 | 7/1979 | Maldonado et al. | 364/563 |
| 4,406,015 | 9/1983 | Koga | 378/50 |
| 4,577,338 | 3/1986 | Takahashi et al. | 378/207 |

FOREIGN PATENT DOCUMENTS

| | | | |
|---|---|---|---|
| 0168579 | 12/1981 | Japan | 378/207 |
| 0168314 | 9/1984 | Japan | 378/50 |

*Primary Examiner*—Craig E. Church
*Assistant Examiner*—Charles Wieland
*Attorney, Agent, or Firm*—Lilling & Greenspan

[57] ABSTRACT

Improved calibration standard construction for X-ray fluorescence thickness measurement gauges formed of one or more plated layers of known character and thickness disposed on an apertured supporting foil base and accessible to X-radiation through an aperture at the base of a conically shaped bore in a surrounding protective housing member.

7 Claims, 3 Drawing Figures

CALIBRATION STANDARD FOR X-RAY FLUORESCENCE THICKNESS

This invention relates to calibration standards for radiation type thickness measuring equipment and particularly to an improved construction for calibration standards for X-ray fluorescence thickness measuring gauges and to methods of making the same.

X-ray fluorescence thickness measuring gauges of the general type illustratively depicted in U.S. Pat. Nos. 2,711,481, 4,162,528 and 4,406,015 are commercially utilized in the nondestructive measurement of the thickness of thin coatings on base substrates of differing material. In such field of usage, the X-ray fluorescence gauge is generally calibrated for measurement of particular material and thickness ranges by precedent calibration with actual plated samples of varying but known thickness of the specific coatings to be later measured. One expedient heretofore employed for such precedent calibration, and particularly where the specific plated or otherwise coated thickness standards are not available, was to adhesively secure a discrete mechanically fabricated foil, as obtained by rolling or the like, to a base substrate sample. However, in the lower thickness ranges such mechanically produced foils, if available at all, are extremely fragile and are difficult to utilize without attendant deterioration or damage thereto. Moreover, many industrial coatings or platings can be of a thickness well below that obtainable by such mechanically produced foils with the attendant difficulty in extrapolating the calibration data and ultimate lack of measurement certainty. Another expedient heretofore employed was to plate a sample of a specific coating to be later measured on to a base substrate of the same material that would conform to that of the later measured product.

This invention may be briefly described as an improved construction for calibration standards for X-ray fluorescence thickness measurement gauges and similar apparatus and a method of making the same. In its broad aspects, the subject invention includes the provision of one or more discrete plated coatings of desired and known thickness on a substantially thicker supporting foil substrate; the mounting of such composite plated substrate in a rigid housing structure; and selectively removing a small area of said supporting foil substrate to expose the surface of the plated coating previously disposed in interfacial relation with said supporting foil. In its narrower aspects, the subject invention includes the provision of a selectively contoured housing structure to facilitate selective use of the exposed portion of the single or multilayer plated layer in association with any appropriate base material that conforms to the actual product to be later measured.

Among the advantages of the subject invention is the provision of rugged and durable thickness standards for calibration of X-ray fluorescence thickness measuring gauges and which will permit the ready utilization of the so-formed standard with any base substrate material conforming to the product to be later measured.

The object of this invention is the provision of an improved construction for calibration standards for X-ray fluorescence thickness measuring apparatus.

Other objects and advantages of the subject invention will become apparent from the following specification and claims and from the appended drawings which illustrate, in accord with the mandate of the patent statutes, a presently preferred embodiment of a calibration standard incorporating the principles of this invention.

Referring to the drawings.

For convenience the sequential steps of fabricating the improved calibration standard will be individually described with the final steps therein resulting in the improved unit.

Figure 1:
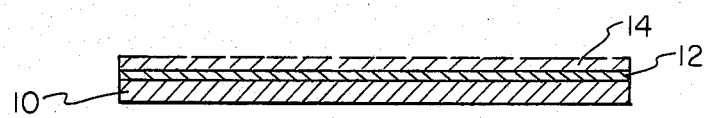
FIG. 1 is a schematic vertical section through a partially formed multilayer subcomponent embodying the principles of this invention.

Referring to FIG. 1, the improved calibration standard is fabricated by initially plating or otherwise depositing a thin first layer 12 of substantially uniform and known thickness of the particular metal to be later measured on the surface of a much thicker mechanically formed supporting foil 10. By way of illustrative example, the supporting foil 10 may suitably comprise a ½ to ¾ inch diameter round piece of rolled copper foil of 0.0005 to 0.001 inches in thickness. Other perimetric shapes such as a square or the like could be employed, if desired. The thickness of the deposited first layer 12 could be of approximately the same thickness as, or a predetermined known amount different from, the thickness of the coating to be ultimately measured and will, in most cases, be appreciably thinner than the thickness of the supporting foil 10.

If the ultimate material to be measured includes a multilayer combination of plated or deposited metals, such as a plating of gold on top of a plating of nickel, i.e.-Au/Ni, the first plated layer 12 would then be constituted of a known thickness of plated nickel and the second layer 14 would be constituted of a known thickness of gold, plated or otherwise deposited thereon, as indicated by the dotted lines, to provide a second discrete layer of known thickness of different metal.

By way of illustrative example, a suitable multilayer standard could include a supporting foil 10 of 0.001 inch thickness, a plated nickel layer 12 of about 50 microinches in thickness, and an overlying gold layer 14 of about 20 microinches in thickness. In another illustrative example, the plated layer 10 could constitute a tin-lead mixture varying from 60/40 to 90/10 [Sn/Pb] having a thickness of from 100 to 1000 microinches.

Figure 2:
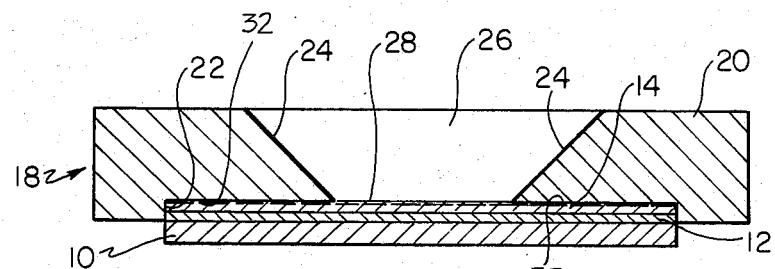
FIG. 2 is a schematic vertical section illustrating the incorporation of the subcomponent of FIG. 1 in a selectively contoured house member.

As shown in FIG. 2, the supporting foil 10 having the first layer 12 deposited thereon or having a multilayer plating 12/14 deposited thereon is then mounted on a selectively contoured housing member, generally designated 18. The housing member 18 suitably comprises a disklike element 20 having a truncated conical bore 26 with the dependent end of the inwardly sloping sidewalls 24 thereof defining a circular aperture 28. The disklike element 20 may be slightly undercut beneath the aperture 28 to provide a shallow recess 22 suitably shaped and sized to accommodate the supporting foil 10 having the plated layer 12 or the plated multilayers 12/14 on the surface thereof. The perimetric portion 30 of the plated foil specimen is adhesively or otherwise secured to the adjacent and interfacial contiguous surface 32 on the underside of the disk element 20 so as to form a monolithic assembled structure with the plated layer 12 or plated multilayers 12/14 positioned for exposure to radiation through the conical bore 26 and aperture 28.

By way of specific example, the disklike element 20 may suitably be a disk of 1 to 1½ inches in diameter and from 1/16th to ¼th inch thick and may be formed of any rigid material.

Figure 3:
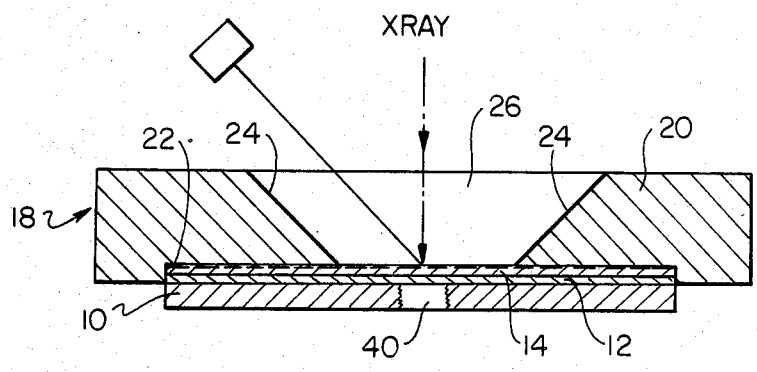
FIG. 3 is a schematic vertical section through a completed multilayer calibration standard incorporating the principles of the invention.

As shown in FIG. 3, a small portion of the supporting foil 10, preferably disposed coaxial with the axis of the conical bore 26, is selectively removed, either before or after mounting in the housing 20, as by electrolytic stripping or by selective chemical dissolution, to provide a small diameter axial bore 40 therethrough that serves to expose the undersurface of the first plated layer 12. By way of specific example, such bore 40 can be about ⅛th inch in diameter.

As will now be apparent, the finished structure of the calibration standard, as illustrated in FIG. 3, is essentially monolithic in character with the operationally critical plated layers 12 or 12/14 only being exposed at the bottom of the conical bore and within the bounds of the aperture 28. The plated layer 12 is also exposed at the base of the bore 40 in the supporting foil 20. However, both such locations are remote from the exterior surface of the unit and will be effectively insulated from contact during normal usage thereof. The composite finished structure is thus sufficiently rugged as to permit easy handling of the calibration standard and yet to minimize damage to the critical plated coatings thereon during normal usage. The particular materials employed in the disclosed calibration standard and the materials utilized for the supporting foil 10 and the deposited layer 12 and/or the deposited overlayer 14, if such is included, will, of course, be determined by the nature of the actual materials on which the ultimate measurements are to be taken.

As will be now also apparent to those skilled in this art, the resulting calibration standard is both rigid and rugged in construction with an area of typically only about ⅛th inch diameter of the critical deposited underlayer 12 that is not backed up by the protective supporting foil 10. The improved calibration standard, as illustrated in FIG. 3, can be readily placed upon any sample of base material to provide the desired coating/base material calibration standard. Of particular interest are multilayer, i.e. layers 12/14, thickness standards, typically, for example, gold on nickel as above noted, which is commonly plated on a number of different base materials such as for example, copper, copper alloys, phosphor, bronze, nickel alloys and the like.

Having described our invention, we claim:

1. A calibration standard for X-ray fluorescence thickness measuring equipment comprising
   a supporting foil of a first metal having a small diameter bore therethrough,
   a first layer of uniform known thickness of a second and different metal deposited on one surface of said supporting foil and overlying the bore therein,
   a housing member disposed in perimetrically secured relation with the marginal edges of said supporting foil and overlying said first layer deposited thereon,
   said housing member including an inwardly directed bore that terminates in an aperture adjacent the surface of said first layer for selective exposure of the portion of said first layer overlying the small diameter bore in the supporting foil to incident X-radiation.

2. The calibration standard as set forth in claim 1 wherein said small diameter bore in said supporting foil is coaxial with the bore in said housing member.

3. The calibration standard as set forth in claim 1 wherein said housing member is adhesively secured to the marginal edges of said supporting foil.

4. The calibration standard as set forth in claim 1 wherein said inwardly directed bore in said housing member is of converging conical configuration.

5. The calibration standard as set forth in claim 1 including a second layer of uniform known thickness of a third and different metal deposited in overlying relation with said first layer and exposable to incident X-radiation through said bore in said housing member.

6. In the formation of calibration standards for X-ray fluorescence thickness measuring equipment the steps of
   depositing a thin continuous layer of uniform thickness of a first metal upon the surface of a foil of second and different metal that is of greater thickness than said deposited first metal layer,
   removing a portion of said supporting foil to form a bore therein to expose the undersurface of said deposited metal layer thereon,
   and perimetrically securing said foil to a housing member having a bore therein disposed in coaxial alignment with the bore in said supporting foil and with said deposited metal layer being disposed in transverse covering relation with the dependent end of said bore in said housing member.

7. The method as set forth in claim 6 including the step of depositing a thin layer of uniform thickness of a third metal upon the surface of said first metal layer prior to securing said foil to said housing member.

* * * * *